May 20, 1952 G. MERRILL Plant Pat. 1,099

PEACH TREE

Filed Oct. 27, 1950

WITNESS

Addison E. Avery

INVENTOR

Grant Merrill

Webster & Webster

ATTYS.

Patented May 20, 1952

Plant Pat. 1,099

UNITED STATES PATENT OFFICE 1,099

PEACH TREE

Grant Merrill, Red Bluff, Calif.

Application October 27, 1950, Serial No. 192,553

1 Claim. (Cl. 47—62)

This invention is directed to a new and distinct variety of peach tree which bears late ripening, yellow-fleshed freestone fruit.

The present variety of peach tree was originated by me in the breeding plot which I maintain on my farm near Red Bluff, California. Seeds of the Kirkman Gem peach (U. S. Plant Patent No. 506) were planted on the above breeding plot in February, 1946. The parent tree of the instant variety first fruited in September, 1948.

Among a number of seedlings the present variety was noted as being especially outstanding, by reason of several distinctive characteristics, as will hereinafter appear, in comparison to the parent, Kirkman Gem.

Subsequent to its discovery, this variety was cleft grafted onto mature Golden Jubilee trees in my orchard near Red Bluff, California, and the reproductions have since come into bearing; such reproductions retaining in full the novel characteristics of the parent tree, and its fruit.

The present variety of peach tree and its fruit generally resembles the Kirkman Gem, including the ability of the flesh of the fruit not to darken or oxidize detrimentally when exposed to the air, but distinguishes advantageously from the Kirkman Gem in the following respects:

Firstly, the fruit of the present variety ripens a few days later than the Kirkman Gem; the first picking being near the middle of the Kirkman Gem harvest and continuing some days therebeyond.

Additionally, the fruit of the instant variety is more red in skin color; the fruit does not have a soft stripe down the suture, as does the Kirkman Gem; and the fruit is more elongated or "Elberta" shaped, preferred by many on the market.

A further distinguishing feature is that the fruit of the present variety is firmer at the shipping stage of ripeness, and thus less subject to deterioration in transit.

With respect to the tree, the present variety is stronger growing, and more vigorous than the Kirkman Gem.

Figure 1:
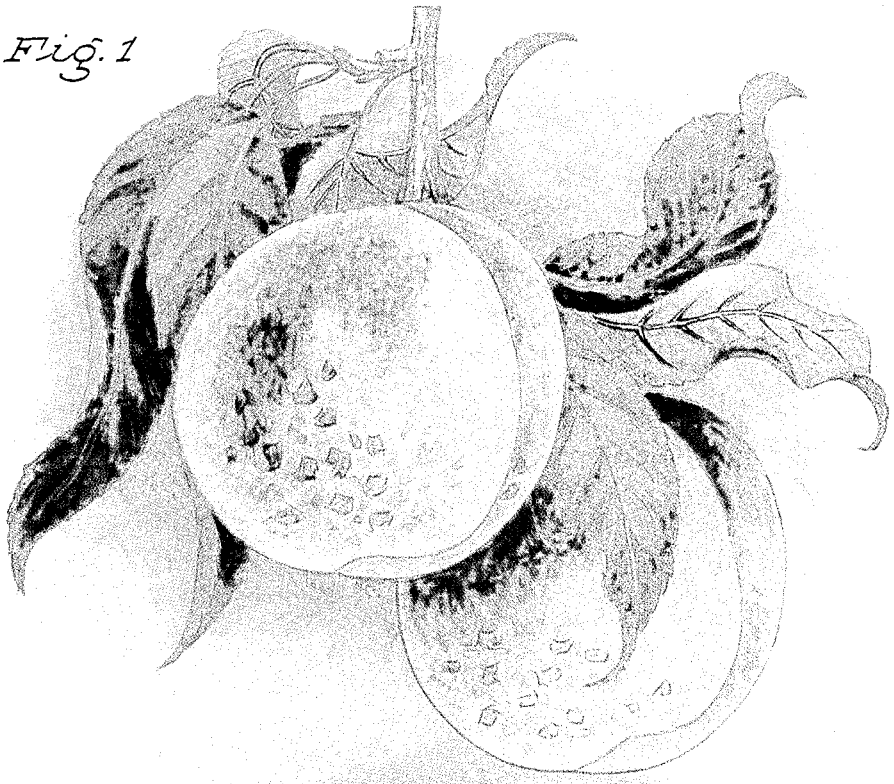
Fig. 1 is a perspective view of the fruit in connection with a twig and leaves.
Figure 2:
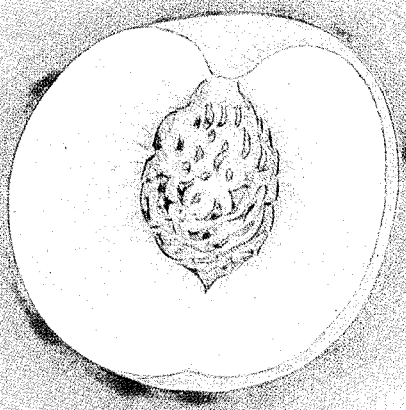
Fig. 2 is a sectional view of the one of the fruit, with the stone exposed.

Referring now more specifically to the promological details of the new and distinct variety of peach tree, the following is an outline description thereof; all major color plate identifications being by reference to Maerz and Paul Dictionary of Color.

Tree: Medium size; medium shape; vigorous; vase formed; productive; regular bearer; medium stocky; medium shaggy.

Trunk: Medium stocky; medium shaggy.

Branches: medium stocky; medium shaggy; reddish brown; medium dull.

*Lenticels.*—Medium quantity; medium size.

Leaves: Average length—6"; average width—1¼". Medium size; lanceolate; acutely pointed; smooth. Color—top side: medium green (22–L–6); under side: slightly lighter green (22–K–3).

*Leaf twigs.*—Light brown (15–J–12), shading to green along one side.

*Margin.*—Crenate.

*Petiole.*—Medium length; medium thick.

*Glands.*—None to ten—average, six. Alternate; small to medium size; reniform. Green to yellowish-green, mostly on leaf blade, some on petiole.

*Stipules.*—On new growth—drop off early.

Flower buds: Medium size; medium length; obtuse; free; pubescent.

Flowers: First bloom—March 5, 1950; full bloom—March 14, 1950. Early blooming; large size; pink.

Fruit: Maturity when described—eating to firm ripe. Dates of first and last picking—September 15, 1950, and September 29, 1950. Size—uniform, large. Average diameter axially—3⅛"; average transversely in suture plane—2⅞"; average cheek to cheek—2¾".

*Form.*—Mostly uniform; symmetrical; globose to oblong.

*Suture.*—Distinct; shallow; extends from base to beyond apex. Slight depression beyond pistil point.

*Ventral surface.*—Slightly lipped throughout, but more on right. Lips unequal.

*Cavity.*—Rounded; abrupt; slightly elongated in suture plane, with suture showing on one side. Average depth—$\frac{5}{16}$"; average breadth—1⅜". Markings—yellow undercolor, with red blush where exposed to sun.

*Base.*—Retuse.

*Apex.*—Short; truncate to retuse.

*Pistil point.*—Apical.

Skin: Thin; medium tender; free when soft; no tendency to crack.

*Color.*—Bright yellow under-color (11–H–8), some red blush (7–L–9) over almost entire fruit. Red dapple (5-F-11) over three-fourths of fruit.

*Down.*—Scant, rolls slightly when rubbed.

Flesh:

*Color.*—Yellow (9-L-7), flecked with red (4-L-6) half way from pit to skin. Almost solid red next to stone.

*Surface of pit cavity.*—Red with creamy pink fibers.

*Amygdalin.*—Wanting.

*Juice.*—Moderate; rich.

*Texture.*—Firm; meaty.

*Fibers.*—Abundant; fine; tender.

*Ripens.*—Evenly.

*Flavor.*—Mild; sub-acid; delicate.

*Aroma*—Distinct.

*Eating quality.*—Excellent, where preference is to acid flavor and high aroma rather than sweetness.

Stone: Free, adheres to flesh slightly on dorsal edges.

*Fibers.*—Short, retaining a few short fiber-like threads.

*Size.*—Medium. Average length—$1\frac{1}{2}''$. average breadth—$1\frac{5}{16}''$; average thickness—$\frac{9}{16}''$.

*Form.*—Obovate to acuminate.

*Base.*—Slightly oblique to straight.

*Hilum.*—Oval.

*Apex.*—Acuminate.

*Sides.*—Mostly equal.

*Surface.*—Irregularly furrowed near base and toward apex.

*Ridges.*—Rounded.

*Pits.*—Circular to elongated.

*Ventral edge.*—Thick, without wing.

*Dorsal edge.*—Full, toward base.

*Ridges.*—On either side; interrupted.

*Color.*—Light tan (14-A-12) stained with reddish purple.

*Tendency to split.*—Slight.

Use: Market; local; dessert; cullinary; canning; freezing; long distance shipment.

Keeping quality: Good.

Shipping quality: Excellent.

The tree and its fruit herein described may vary in slight detail due to climatic and soil conditions under which the variety may be grown.

Having thus described my invention, I claim:

A new and distinct variety of peach tree, substantially as described and illustrated, characterized by its general resemblance to the Kirkman Gem, including late ripening, yellow-fleshed freestone fruit, but distinguished therefrom by a tree which is stronger growing and more vigorous, and by fruit having a first picking a few days later than the beginning of the Kirkman Gem harvest and a last picking subsequent to the termination of such harvest; the fruit being further characterized by skin having more red color, the absence of a soft stripe down the suture, more elongated or "Elberta" shaped, and firmer at the shipping stage of ripeness.

GRANT MERRILL.

REFERENCES CITED

The following references are of record in the file of this patent:

UNITED STATES PATENTS

| Number | Name | Date |
|---|---|---|
| Pl. Pt. 920 | Kirkman | Feb. 7, 1950 |